United States Patent
Shaw (10) Patent No.: US 7,284,554 B2
(45) Date of Patent: Oct. 23, 2007

(54) CONTINUOUS POSITIVE AIRWAY PRESSURE DEVICE

(75) Inventor: Geoffrey Mark Shaw, Christchurch (NZ)

(73) Assignee: Lifevent Limited, Dunedin (NZ)

( * ) Notice: Subject to any disclaimer, the term of this patent is extended or adjusted under 35 U.S.C. 154(b) by 709 days.

(21) Appl. No.: 10/473,952

(22) PCT Filed: Apr. 9, 2002

(86) PCT No.: PCT/NZ02/00057

§ 371 (c)(1),
(2), (4) Date: Sep. 30, 2003

(87) PCT Pub. No.: WO02/089886

PCT Pub. Date: Nov. 14, 2002

(65) Prior Publication Data

US 2004/0107964 A1    Jun. 10, 2004

(30) Foreign Application Priority Data

| Apr. 12, 2001 | (NZ) | ................................. 511096 |
| Sep. 19, 2001 | (NZ) | ................................. 514278 |
| Oct. 29, 2001 | (NZ) | ................................. 515104 |

(51) Int. Cl.
*A61M 16/00* (2006.01)
(52) U.S. Cl. .................. 128/205.13; 128/205.16; 128/204.18
(58) Field of Classification Search ........................... 128/205.13–205.18, 203.11, 202.28, 202.29, 128/911–912, 202.27, 207.12, 204.18; 222/27
See application file for complete search history.

(56) References Cited

U.S. PATENT DOCUMENTS

| 3,754,550 A | 8/1973 | Kipling |
| 3,890,967 A * | 6/1975 | Elam et al. ............ 128/205.17 |
| 4,020,834 A * | 5/1977 | Bird ....................... 128/204.25 |
| 4,452,241 A * | 6/1984 | Sarnoff et al. .......... 128/204.18 |
| 4,667,669 A | 5/1987 | Pasternack |
| 4,836,198 A * | 6/1989 | Gates ..................... 128/205.18 |
| 4,852,564 A * | 8/1989 | Sheridan et al. ........ 128/202.27 |
| 4,941,469 A * | 7/1990 | Adahan .................. 128/205.18 |
| 5,109,833 A * | 5/1992 | Frimberger ................... 601/41 |
| 5,345,929 A * | 9/1994 | Jansson et al. ......... 128/205.13 |
| 5,383,449 A * | 1/1995 | Forare et al. ........... 128/205.11 |
| 5,645,047 A * | 7/1997 | Akers ..................... 128/201.28 |
| 5,787,880 A * | 8/1998 | Swanson et al. ........ 128/202.28 |
| 6,701,926 B2 * | 3/2004 | Olsen et al. ............ 128/207.11 |
| 7,106,955 B2 * | 9/2006 | Thudor et al. .............. 392/394 |

FOREIGN PATENT DOCUMENTS

| DE | 37 12 389 A1 | 10/1988 |
| DE | 41 07 666 A1 | 9/1992 |
| EP | 0 744 184 A1 | 11/1996 |
| SU | 459243 | 4/1975 |

* cited by examiner

*Primary Examiner*—Justine R. Yu
*Assistant Examiner*—Kristen Matter
(74) *Attorney, Agent, or Firm*—McCormick, Paulding & Huber LLP (57) ABSTRACT

A continuous positive pressure device which includes an air reservoir connected to a delivery device (e.g. mask or mouthpiece) by an air supply hose; the reservoir includes a rigid protective housing and a plate which applies uniform pressure on the reservoir irrespective of its degree of inflation; the plate is connected to the housing by a non distorting and expandable frame which can expand or contract to permit movement of the plate only in a single plane, as the reservoir inflates or deflates.

35 Claims, 8 Drawing Sheets

CONTINUOUS POSITIVE AIRWAY PRESSURE DEVICE

TECHNICAL FIELD

The present invention relates to a continuous positive airway pressure (CPAP) device, i.e. a device for supplying air or (more usually) an air/oxygen mixture at a positive (i.e. above atmospheric) pressure, to a patient, and to an air reservoir apparatus for such a device. A CPAP machine may assist the lung function of a sick or injured patient by supplying air, generally oxygen enriched, at an above-atmospheric pressure, and/or may actively assist carbon dioxide removal from the lungs by using two levels of positive pressure. In the latter mode, the device functions as a ventilator and is capable of providing up to 100% of a patient's minute ventilation.

BACKGROUND ART

A number of continuous positive airway pressure devices are already known. Devices of this type currently being used in hospitals in first world countries generally require the supply of oxygen at high flow rates; since most modern hospitals have oxygen on tap and oxygen is available cheaply, a relatively wasteful use of oxygen is acceptable. However, in less developed countries or in out-of-hospital situations, (e.g. in ambulances, on battlefields, in emergency treatment stations) oxygen is available only in cylinders and a high rate of use of oxygen is unacceptable:—the cylinders simply are emptied too quickly.

It is therefore an object of the present invention to provide a continuous positive airway pressure device capable of operating at low flow rates of oxygen, whilst nevertheless reliably supplying the required air/oxygen mix to a patient.

In order to reduce the rate of the use of oxygen, it is necessary to use a reservoir built into the device. This is because the peak gas flow requirements of patient in acute respiratory distress can be anything from 60-120 liters per minute but practical engineering considerations mean that the gas flow rate through a portable continuous positive airway pressure device should be kept below 30 liters per minute. To make up the difference between gas demand and gas supply, portable devices must employ a storage system to store the gas while the patient is in between breaths or is breathing out. Any such storage system must be capable of a substantially constant pressure response, i.e. the pressure of the gas supply to the patient must not vary substantially whether the reservoir is full, part full or nearly empty.

A number of existing devices use a balloon reservoir made of elastic material or a reservoir shaped like an old-fashioned fire side bellows. Both of these designs have the drawback that the pressure of the gas supply to the patient varies considerably depending upon whether the balloon/bellows is nearly full, partly full or nearly empty. To overcome this drawback, a very much larger reservoir has to be used than is optimal for a portable device.

Some designs have been proposed to overcome this problem by providing a constant pressure response reservoir; see for example German Patent No.s DE 3712389 and EP 0744184.

German patent No DE 371-2389 discloses a reservoir of flexible material the upper surface of which is weighted either by a weight or by a weighted lever. However, the reservoir does not incorporate any type of stabilizing device to ensure that, as the bellows is compressed and expanded, the weighting on the reservoir is kept even.

EP 0744184 discloses a reservoir at least partly of elastic material, preformed so that the reservoir itself supplies compression to its contents. Since the pressure applied by a reservoir of this design would fluctuate markedly depending upon the volume of gas contained in the reservoir (i.e. according to the degree of expansion of the reservoir) a reservoir of this design could not provide a gas at a uniform or substantially uniform pressure.

A further drawback to both of the above described designs is that they relate to relatively large and complex devices which would be unsuitable for use outside a hospital environment.

Russian patent 459243 and German patent DE 410-7666 both disclose a reservoir in the form of simple bellows which is weighted by an upper moving plate. The moving plate can slide towards or away from a baseplate along fixed vertical guides. The guides are rigid and extend the full height of the expanded reservoir, resulting in a bulky apparatus which cannot be regarded as portable except in a hospital environment.

Indeed, a marked drawback of all known designs is the bulk of the equipment. Some of the devices, of course, are not designed to be portable at all, but even those devices which technically are portable are relatively large, fragile and easily damaged. A device which is classed as "portable" for a hospital environment may nevertheless be completely unsuited to being thrown into the back of a truck or into an aircraft, and may be too bulky to be stored conveniently for emergency use.

DISCLOSURE OF INVENTION

It is therefore a further object of the present invention to provide an air reservoir apparatus which can be incorporated into a continuous positive airway pressure device which can be stowed into a relatively small space and which is robust and easily portable when not in use.

The present invention provides an air reservoir apparatus for a continuous positive airway pressure device, the air reservoir apparatus comprising: a rigid housing protecting an air reservoir; a plate arranged to apply a uniform pressure on the air reservoir, irrespective of the degree of inflation of the air reservoir, said plate being connected to the housing by a substantially non-distortable expandable frame, which can expand or contract to permit movement of the plate only in a single plane, as the air reservoir respectively inflates or deflates.

As used here in, the term "air" includes air, oxygen, air/oxygen mixtures and mixtures of air and/or oxygen with other gases and with therapeutic drugs or gene therapy or other preparations.

Preferably, the plate is formed as one side of the housing, so that when the air reservoir is deflated, the plate can be secured to the housing to completely enclose the air reservoir. The plate may be a solid sheet of material or, if it is not necessary for the plate to be dust proof, may be formed from a rigid mesh or other openwork material.

Preferably also, the air reservoir is made of a flexible non-elastic material.

The present invention further provides a CPAP device incorporating the above-described air reservoir apparatus connected by an air supply hose to a delivery device.

Gas supply to the device of the present invention can be delivered by any suitable gas delivery system, which includes, but is not limited to:—compressed air and/or oxygen from a piped system or from a cylinder; fan forced air and/or oxygen, supplied by any of a range of known equipment; compressed air/oxygen from a portable reservoir. It should be noted that a portable reservoir can be devised from any large capacity inflatable object, even one which is hand pumped e.g. an inflatable mattress.

The device may be used with standard bore hose (internal diameter approximately 22 mm). However, it is preferred to use the device of the present invention with a wide bore hose (i.e. a hose of diameter between 30-55 mm internal diameter), since the combination of the device and wide bore hose provides apparatus in which the imposed work of breathing on a patient is independent of the fresh gas flow rate.

A further aspect of the present invention is that the above described device, used in combination with wide bore hose, may be used to deliver drug therapy and gene therapy, and hyperbaric treatments, and to provide portable CPAP to treat altitude sickness and acute pulmonary oedema (e.g. heart failure and lung injury).

The device also is useful in intra-/post-operative applications where the patient has an increased oxygen requirement, (typically due to small areas of lung collapse). Further, the device is useful in the treatment of all cases of chronic airflow limitation or chronic airways disease (e.g. asthma).

For emergency/battlefield use, the device may be fitted with chemical absorbent or bacterial/viral/other biologically active particle filters, to protect the patient from toxic gases and/or biological weapons.

BRIEF DESCRIPTION OF THE DRAWINGS

By way of example only, a preferred embodiment of the present invention is described in detail with reference to the accompanying drawings, in which:—

BEST MODES OF CARRYING OUT THE INVENTION

Figure 1:
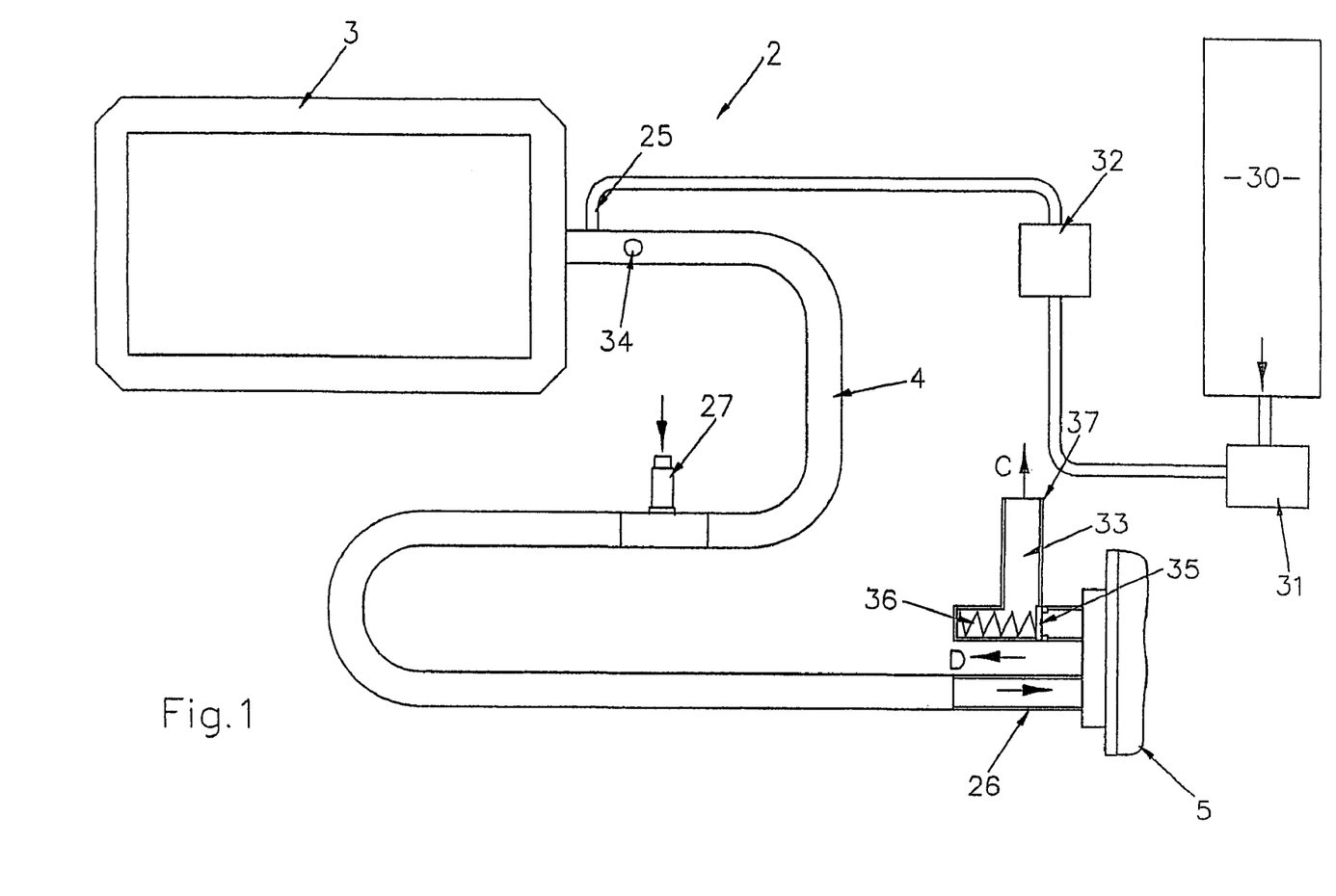
FIG. 1 is a diagrammatic plan view of the device of the present invention set up for use.

Referring to FIG. 1 of the drawings, a device 2 in accordance with the present invention comprises an air reservoir apparatus 3 (shown in outline only), which in use is connected by an air supply hose 4 to a delivery device in the form of a facemask 5. The facemask 5 may be of any suitable known type and does not form part of the present invention.

Different delivery devices may be used, depending upon the circumstances. For example the delivery device may be a nasal mask or a mouthpiece (optionally in combination with a nasal clip) or even an endotracheal or tracheotomy tube.

Figure 2:
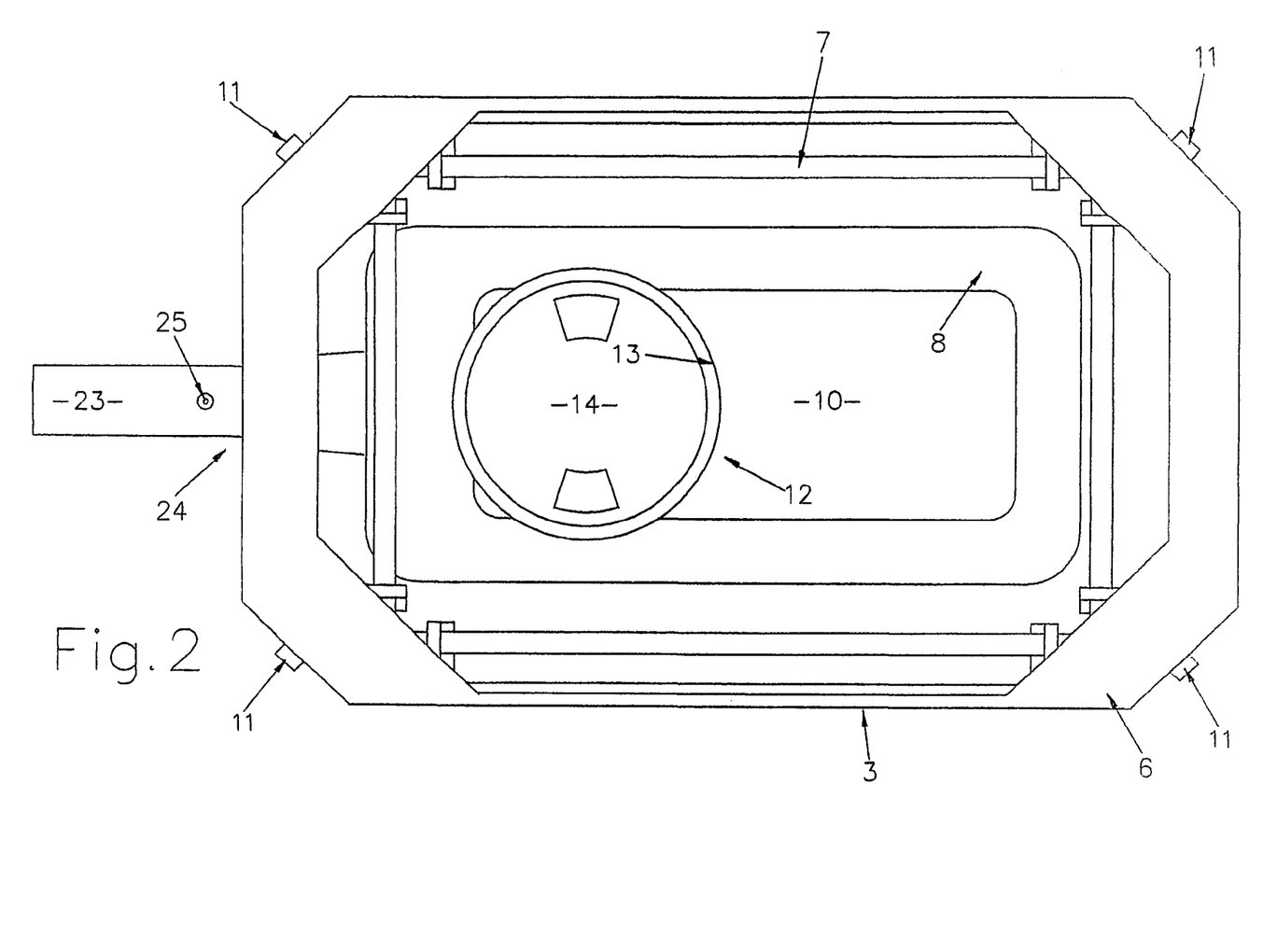
FIG. 2 is a plan view of part of the device of FIG. 1 on an enlarged scale.

The air reservoir apparatus 3 is shown in greater detail in FIGS. 2-5. The apparatus 3 comprises a housing 6 which contains a support framing 7 surrounding an air reservoir 8. The housing 6 is in the form of a shallow rectangular case with parallel, opposed flat sides 9,10. The side 10 is formed separately from the rest of the housing, and is secured to the housing only by the support framing 7 and by four catches 11 located at the corners of the housing (FIG. 2 only).

Figure 4:
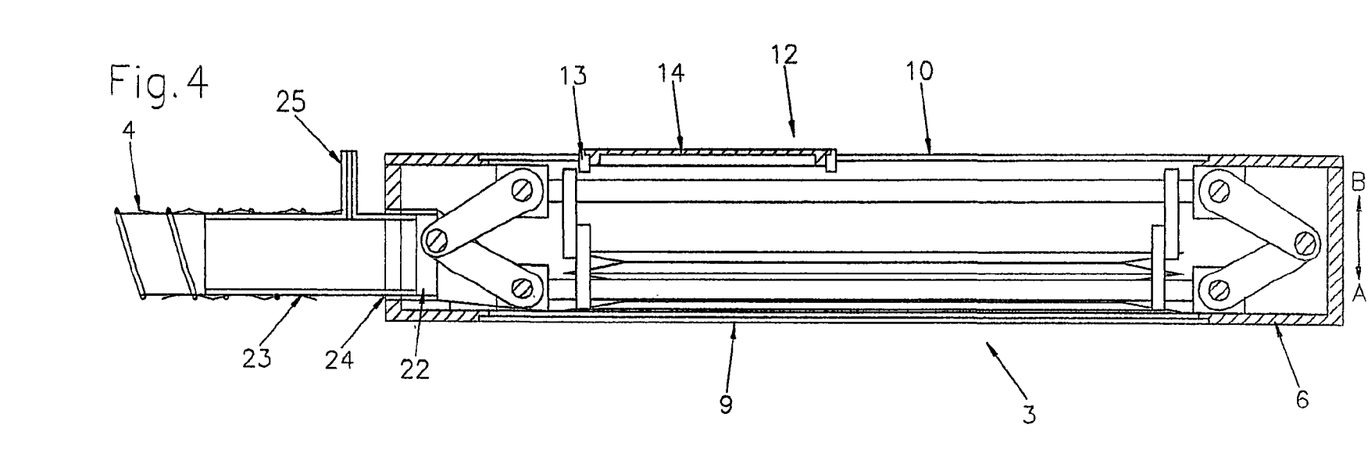
FIGS. 4 and 5 are sectional side views through the device of FIG. 2, showing the device in use.
Figure 5:
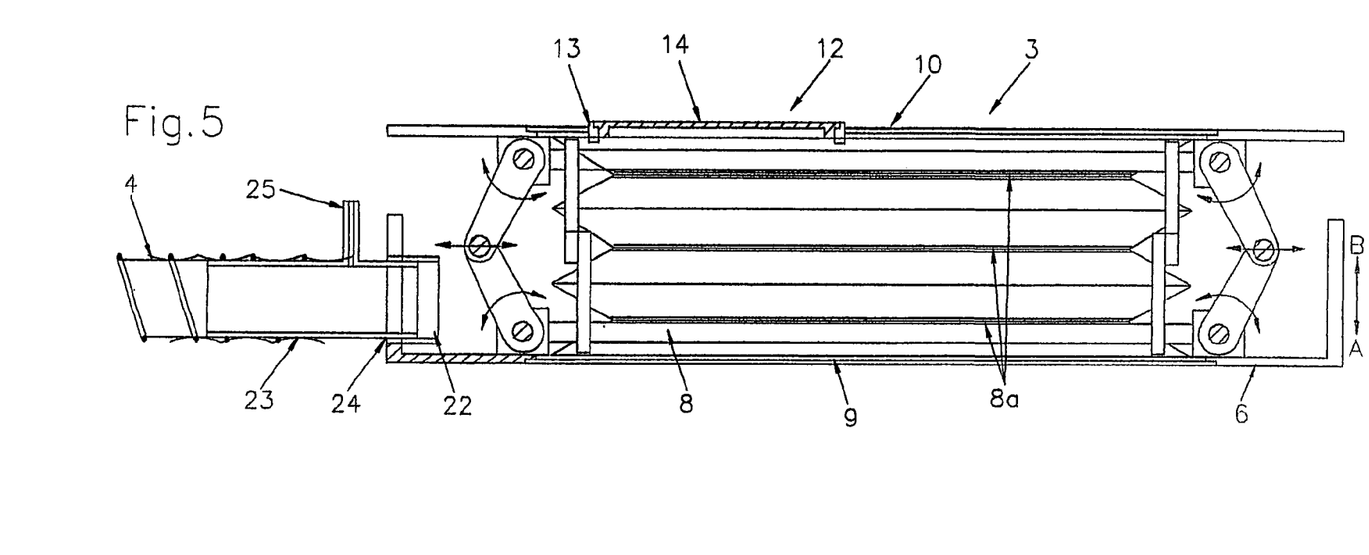

In use, the housing 6 lies flat on side 9 and the catches 11 are released so that the side 10 can move towards and away from the side 9 as indicated by arrows A and B in FIGS. 4 and 5. The housing 6 may be made of any tough, impact resistant, lightweight material; preferably, the sides 9,10 are made of a transparent material.

Figure 6:
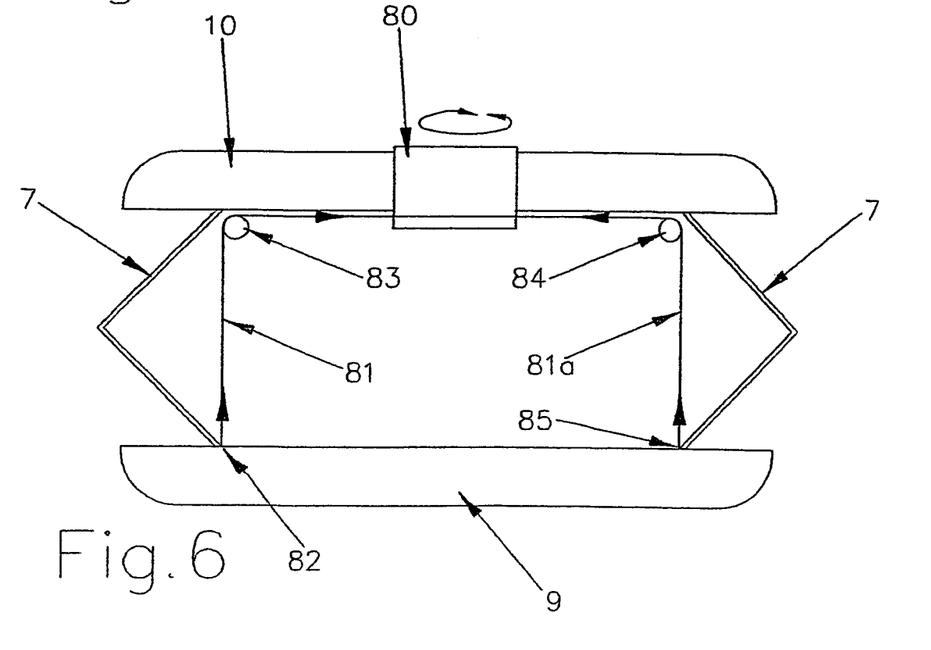
FIGS. 6 and 7 are diagrammatic side and plan views respectively of a preferred weighting device.
Figure 7:
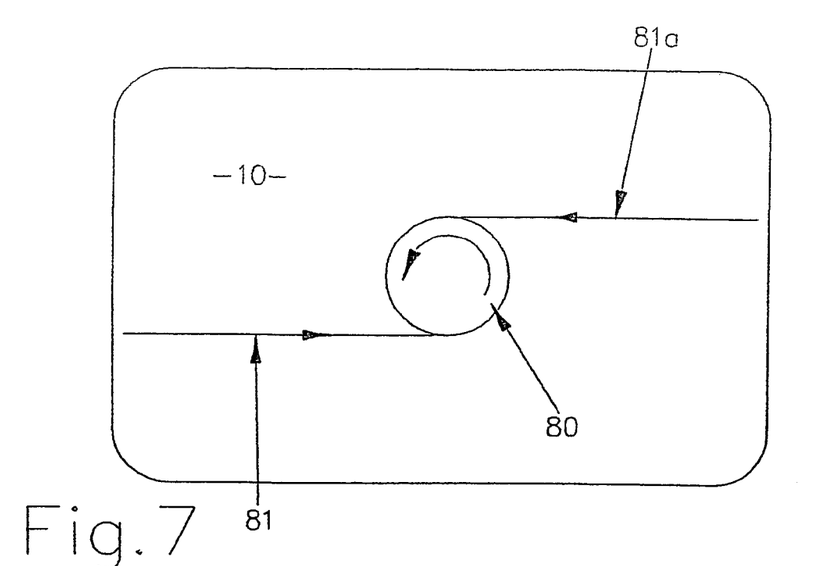

The side 10 is weighted or fitted with removable weights, up to a total weight of about 4 kg. The weighting may be achieved in any convenient manner:—for example, the side 10 could be made of a heavy material and/or could be fitted with weighted strips (not shown) along its edges and/or could be provided with pockets on its upper or lower surfaces into which weights could be inserted. Preferably, the weighting system illustrated in FIGS. 6 and 7 is used, as hereinafter described. However, it is preferable (but not essential) that the side 10 is weighted evenly.

An access port 12 is formed in one of the sides 9,10, to allow access into the interior of the housing 6. The port 12 may be formed in either of the sides 9,10; in the embodiment illustrated, the port 12 is formed in side 10. The port 12 consists of a circular frame 13 which is rigidly secured around the edge of aperture formed in side 10, and a plate 14 which is externally screw threaded to engage a corresponding screw thread formed on the inner surface of the frame 13. When the plate 14 is screwed in place, the port 12 is substantially dust proof.

The support framing 7 connects the movable side 10 to the fixed side 9 in such a way that the movable side 10 can move only in a single plane and at all times during its movement towards or away from the side 9 remains parallel to the side 9. Thus, the support framing 7 must provide a rigid and non-distorting hinge which supports the movable side 10 evenly.

Figure 3:
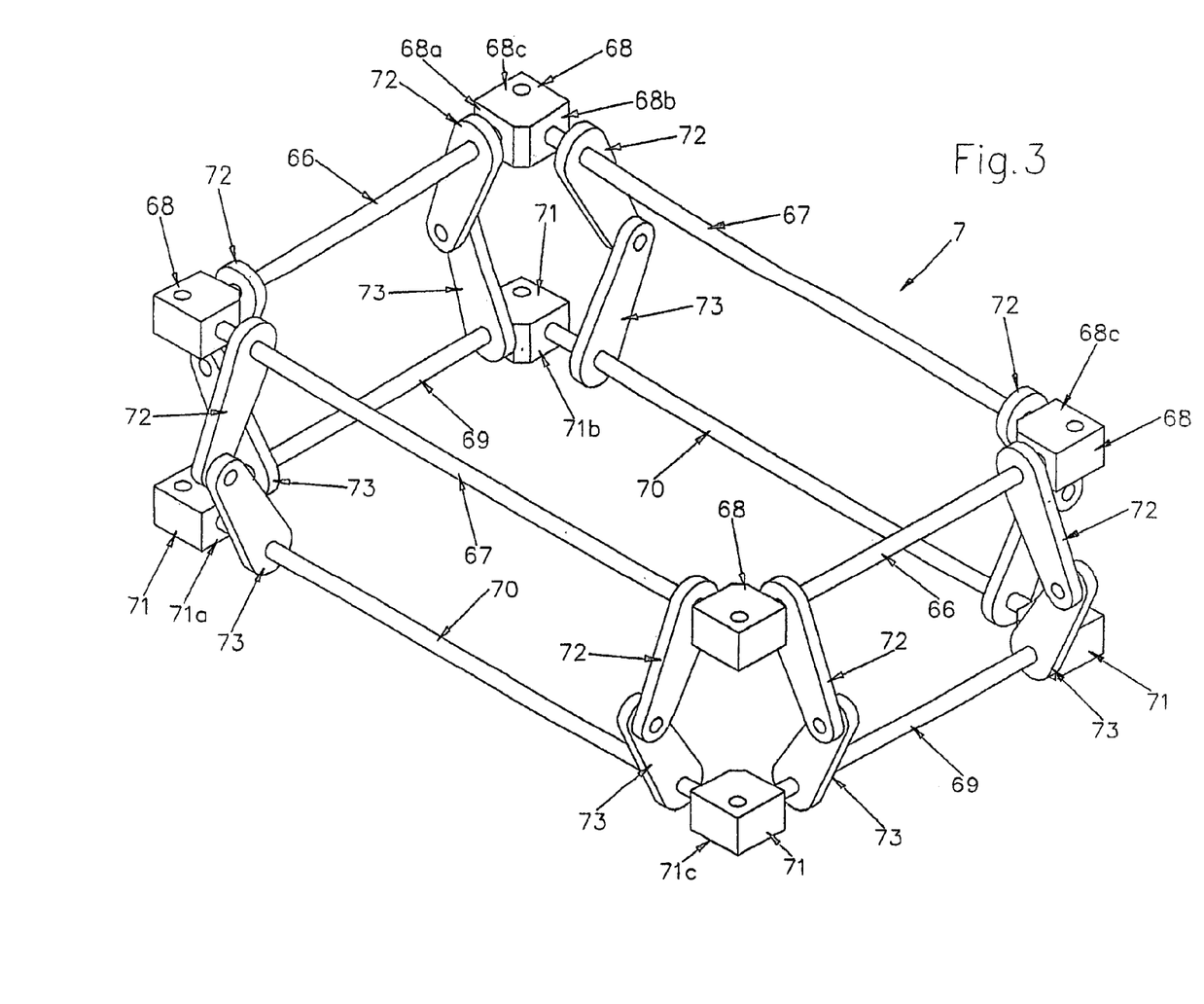
FIG. 3 is an isometric view of the support framing of the device of FIG. 2, on an enlarged scale.

As shown in FIG. 3, the support framing 7 comprises a first rectangular frame made from two pairs of parallel opposed rods 66,67 secured between corner blocks 68, and a second rectangular frame made from two pairs of parallel opposed rods 69,70 secured between corner blocks 71. The first and second frames are spaced apart in a direction perpendicular to the planes of the rectangles, and interconnected by eight pairs of hinge arms 72,73, as hereinafter described.

In the rectangular frames, each of the corner blocks 68,71 comprises a cuboid block with a ball bearing (not visible) set into each of two adjacent sides 68a, 68b, 71a, 71b. The rods, 66,67 of the first frame and the rods 69,70 of the second frame are mounted in the bearings of the corresponding blocks.

The support framing 7 shown in FIG. 3 is mounted between the parallel opposed sides 9,10 of the air reservoir apparatus housing (see FIGS. 4 and 5) with the side 10 rigidly secured to the upper surface 68c of each of the blocks 68, and the side 9 rigidly secured to the lower surface 71c of each of the blocks 71.

Each pair of hinge arms 72,73 consists of a flat plate which is pivotally mounted on the corresponding rod at one end, and pivoted to the other hinge arm at the other end. Each pair of hinge arms 72,73 is mounted between the first and second frames adjacent the blocks 68,71. Each pair of arms is formed with a stop (not shown) to prevent the hinge from over extending i.e. moving to, or close to, a position in which the two plates of the hinge lie in the same vertical line, since this would jam the hinge and prevent it from collapsing.

In use, the support framing 7 provides a rigid and non-distorting hinge which connects the movable side 10 to the fixed side 9 in such a way that the movable side 10 can move only in a single plane and at all times during its movement towards or away from the side 9 remains parallel to the side 9. The pairs of hinge arms 72/73 maintain the first frame in a plane parallel to that of the second frame at all times during movement, and the arrangement of two pairs of hinge arms between each opposed pair of rods in the first and second frames prevents any swaying or distortion of one frame relative to the other.

The configuration and arrangement of the frame 7 described above will expand and contract easily, with minimal friction. Further, because the frame 7 is braced at each corner by the blocks 68, 71, the frame will not distort or wobble even when fully extended as shown in FIG. 5. This stability is very important, because in use the side 10 applies pressure to the air reservoir 8, as hereinafter described, and if the frame 7 distorts or sways to one side or the other, the pressure applied to the reservoir 8 will be uneven. It is important that the frame 7 maintains this stability even when subject to external forces, e.g. when the device is being used in a moving vehicle.

The frame 7 could have a different shape in plan (e.g. triangular or hexagonal) and/or a different cross sectional shape, but it is important that, whatever the shape of the frame, it remains stable and undistorted in all positions.

The air reservoir 8 is a bag made of a flexible but non-extensible sheet material such as Mylar; preferably the material is transparent. The air reservoir 8 is formed with a series of concertina pleats around its edge, so that the collapsed reservoir lies flat, but the expanded reservoir retains its shape. Each of the inner folds 8a of the reservoir is reinforced by the stiffening rib (shown in FIG. 5 only) which extends around the outside of each inner fold, to ensure that the reservoir keeps its shape even when expanded.

It would be possible to build stiffening ribs or other internal support into the air reservoir itself, rather than using separate external ribs.

Instead of, or in addition to, the stiffening ribs, the air reservoir 8 may be held in shape by internal reinforcing webs made of the same material as the reservoir. These webs may be arranged as spaced parallel sheets extending across the width of the reservoir, which are tensioned as the reservoir expands, and so hold it in shape, i.e., the reference numeral 8a in FIG. 5 would represent the internal reinforcing webs rather than the inner folds and stiffening ribs.

By using a non-extensible material to form the reservoir and using a vertically ascending to weight virtually no energy is lost as heat to the reservoir bag. This contrasts with current devices that use rubber materials and/or sprung bellows systems. This therefore minimizes any additional work of breathing imposed by this invention.

The air reservoir 8 has a tubular inlet 22 formed integrally with the bag at the lower surface of one end of the bag. The inlet 22 may be push fated onto a connector tube 23 which is fitted through an aperture 24 in the housing 6. Preferably, however, the inlet 22 is mounted using a mounting clip as shown in FIGS. 8 and 9.

Figure 8:
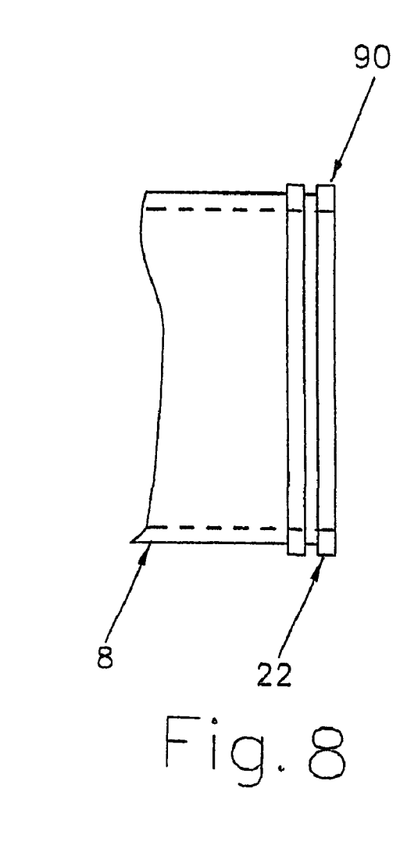
FIG. 8 is an exploded side view of a mounting clip.
Figure 9:
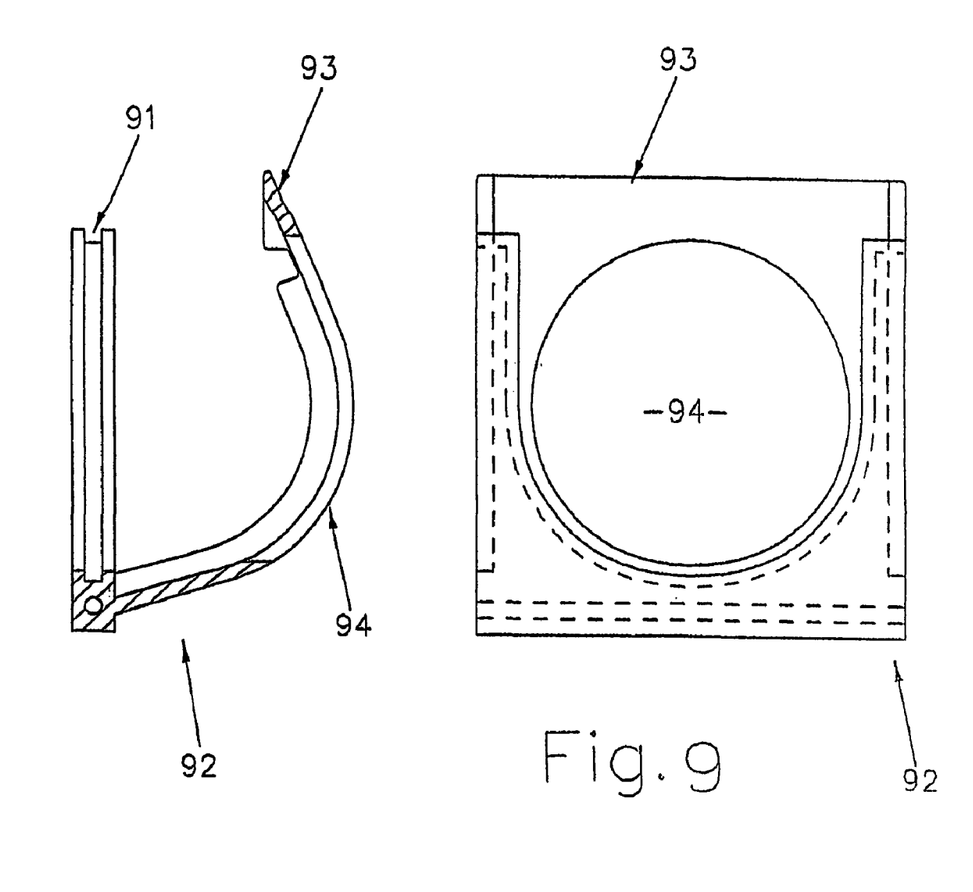
FIG. 9 is a front view of the clip of FIG. 8.

FIGS. 8 and 9 show views of the inlet 22 of the air reservoir 8, with the housing cutaway for clarity. As described above, the inlet 22 is a short tube secured to, or formed integrally with, the air reservoir 8. The inlet 22 is formed with a rim 90 around its outer edge (FIG. 8 only); this rim 90 is pushed fitted into a U-shaped channel 91 formed in one portion of a mounting clip 92.

The mounting dip 92 is also U-shaped in side view:—one arm of the U provides the channel 91, and the other consists of an outwardly convex plate 93 formed with a centre hole 94 of the same diameter as the inlet 22, for access to the inlet 22 by the connector tube 23.

The mounting clip 92 is pivotally mounted in the housing on a pivot (not shown) at the base of the U, such that the clip 92 can pivot between the position of FIG. 8 and a position at 90° to FIG. 8 position. In the position of FIG. 8, the inlet 22 is accessible and can be connected to the connector tube 23. In the position of FIG. 9, the inlet tube is folded flat onto the side 9, with the plane of the inlet 22 and the channel 91 parallel to the plane of the side 9. In this position, the plate 93 dips over the adjacent edge of the side 10 of the housing, to hold the housing closed.

The advantage of the mounting clip 92 is that it reduces the thickness of the housing 6 in the closed position:—the diameter of the inlet 22 cannot be reduced, because this would restrict the flow of gas out of the air reservoir 8. Thus, the housing 6 in the closed position must accommodate the diameter of the inlet 22, resulting in a relatively bulky housing unless the inlet 22 can be turned through 90 degrees by using the clip of the present invention.

The inlet 25 from the oxygen/air supply is formed in the connector tube 23 adjacent the housing 6. The other end of the hose 4 is a push fit on the inlet 26 of the mask 5. The hose 4 is a tough, very light, flexible wire reinforced wide bore hose, preferably made of transparent material; typically, the tube would have a diameter of the order of 41 mm. The wire reinforcing prevents kinking of the hose and allows the hose to be compressed along its length, for compact storage. The use of a wide bore hose is important because this minimizes the pressure drop that occurs with transient high flows during inspiration obviating the need for high fresh gas flows. Hose typically used in present continuous positive airway pressure devices has an internal diameter of 22 mm; thus, comparatively speaking, the wide bore hose used in this invention gives only about $\frac{1}{16}$ of the pressure drop in conventional breathing hoses. As a result the additional work of breathing imposed by the breathing circuit is minimized.

The use of wide bore hose has the further advantage that the device also can be used to deliver to the patient's lungs any agent which can be delivered using metered dose inhaler technology. The agent is delivered through a port 27 in the hose 4. This technique is not limited to agents related directly to the lungs:—providing the product is one which can be absorbed by the lungs, other parts of the body can be treated via systemic absorption.

Agents which can be administered through metered dose inhalation include (but are not limited to) drugs such as bronchodilators, gene therapy agents, and appropriately packaged proteins, peptides and macromolecules.

Metered dose inhaler agents cannot be effectively administered through continuous positive airway pressure devices which operate at high fresh gas flow rates because too high a proportion of the agent is swept straight through the device entrained in the gas, and is not passed through to the patient.

With this invention the fresh gas flow rates may be as low as the patient's minute ventilation which is about 5 to 10 liters per minute.

Rather than simply weighting the side 10 of the device by making it of a heavy material, or fitting it with weighted ships or similar devices, preferably the weighting device shown in FIGS. 6 and 7 is used.

As shown in FIGS. 6 and 7, the side 10 has a springloaded drum 80 mounted in the centre thereof. The drum 80 can be rotated in a clockwise direction to reduce tension and in a is counter clockwise direction to increase tension; preferably, the upper surface of the drum is marked as a dial (not shown) so that a user can select the tension setting required.

A first cable 81 is anchored at one end to a point 82 on the lower side 9 of the housing, led around a pulley 83 secured to the underside of the side 10, and secured to one side of the circumference of the drum 80. A second cable 81a is anchored at one end to a point 85 on the lower side 9 of the housing, led around a second pulley 84 secured to the underside of the side 10 on the opposite side of the drum 80 to the pulley 83, and secured to the opposite side of the circumference of the drum 80. The anchorage points 82, 85 are located vertically below the pulleys 83, 84.

The cables 81, 81a, are made of a tough but non-elastic substance with a high resistance to abrasion (e.g. Kevlar).

The spring loading on the drum 80 tensions the cables 81, 81a; the spring loading is adjusted by rotating the drum 80 as described above. When the air reservoir 8 (not shown) is inflated to move the side 10 away from the side 9, supported by the support framing 7 (shown diagrammatically only), the cables 81, 81a rotate the drum 80 against the force of the spring loading. Thus, the force of the spring loading pulling against the cables 81,81 a pulls the side 10 towards the side 9, acting as an equivalent to weighting the side 10.

The above described device is used as follows:—the housing 6 is supported on its side 9, and the catches 11 are released so that the side 10 is free to move away from the side 9. The weighting on the side 10 (e.g. the loading imposed by the springloaded drum 80) is adjusted in accordance with the level of continuous positive airway pressure required. A higher pressure requires extra weighting. A supply of oxygen (typically from a cylinder 30 at a pressure of 150 atmospheres regulated down to 4 atmospheres at the cylinder outlet) is connected to a Venturi 31 and to a humidifier 32 and then to the inlet 25. The oxygen/air mix admitted through the inlet 25 fills the hose 4 and inflates the air reservoir 8, pushing the side 10 away from side 9, in the direction of Arrow B (FIGS. 4 and 5). The pressure in the reservoir and hose depends upon the back pressure in the system, which is governed by the resistance of the exhaust valve 33. Typically the air pressure in the reservoir is of the order of 5 to 30 cm of water. To avoid over pressuring the system, and causing patient injury, a pressure relief valve 34 is fitted in the hose 4.

The Venturi 31 extrains room air which mixes with the oxygen from the cylinder 30. The mixture may vary between 30% oxygen and 100% oxygen depending upon the patient's condition. Preferably, the Venturi outflow is through a threshold resistor valve set at a level above the CPAP level. The Venturi 31 may be replaced by any of a range of air/oxygen blending devices. However, these blenders require an additional high pressure medical-grade air supply.

The use of a humidifier 32 is optional. However, if a humidifier 32 is used, it may be advisable to heat the hose 4 to prevent condensation as the gases cool along the length of the tube. Current continuous positive airway pressure devices can require fresh gas flows in excess of that which can be adequately humidified. The lower fresh gas flow rates used in this invention allow optimal humidification.

The mask 5 is fitted to the patient in known manner. With the mask 5 in-place, the patient breathes normally. As the patient inhales, the oxygen/air mix flows from the hose 4 through the inlet 26 of the mask 5 and into the patient's lungs. The slight over pressure (i.e. pressure above atmospheric) in the reservoir 8 and hose 4 makes it easier for the patient to breathe and helps to expand the patient's lungs more fully. Further, the additional oxygen in the mix increases the proportion of oxygen available for uptake into the patient's bloodstream.

Because the reservoir 8 is at a substantially constant pressure, this minimizes the pressure drop in the device when the patient inhales.

When the patient exhales, the exhaled gas is expelled through the exhaust valve 33 of the mask 5. The slight over pressure in the hose 4 and reservoir 8 prevents the exhaled gases from passing back into the hose 4. The exhaust valve 33 is of known type and comprises a flap 35 biased into position by a spring 36 to dose the valve against air entering through outlet 37, but to allow exhaled gases to leave through the valve by pressing the flap 35 in the direction of Arrow D, to open the valve passage and allow gas to escape through outlet 37 (Arrow C). The spring 36 is selected to allow the valve to open at a predetermined gas pressure; thereafter, the pressure remains constant and independent of the gas flow.

Because the device of the present invention can be operated at very low flow rates (e.g. 5 liters/min), the consequences of any leaks in the system (whether from defects in the air supply hose or, more commonly, from leaks around the face mast) could be serious to the patient. Preferably, therefore, the circuit includes pressure sensors and audible and/or visual alarms which are triggered if the pressure falls below a predetermined level.

The type of exhaust valve used may be varied to suit specific applications. At low gas flow rates, the use of an exhaust valve which opens on expiration only (e.g. a threshold resistor valve) improves carbon dioxide elimination and reduces the chance of rebreathing. The use of a valve of this type provides a circuit which has the same characteristics as the known "Mapleson A" circuit. The threshold resistor valve sold under the trademark VITAL SIGNS has been found particularly satisfactory for preventing rebreathing.

It should be noted that the fixed orifice valves commonly used by conventional home CPAP systems are not effective at low gas flow rates i.e. gas flow rates of between one and three times the patient's minute ventilation. However, for gas flows greater than 20 liters per minute, a fixed orifice valve is satisfactory; and known types of fixed orifice valves, in combination with known variable flow generation technology, may be used with the device of the present invention.

To replace the air reservoir 8, the plate 14 is removed, and the reservoir detached from the tube 23 and lifted out of the housing 6 through the port 12. The new reservoir is inserted in the same way, connected to the tube 23 and the plate 14 replaced.

Figure 10:
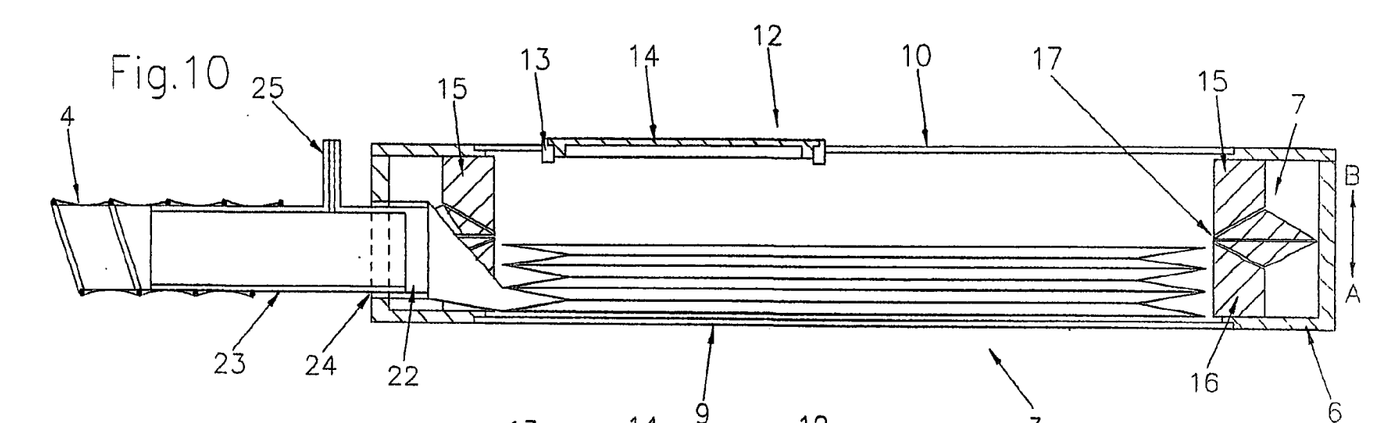
FIGS. 10 and 11 are sectional side views through a device similar to that of FIG. 2, but with a different type of support framing.
Figure 11:
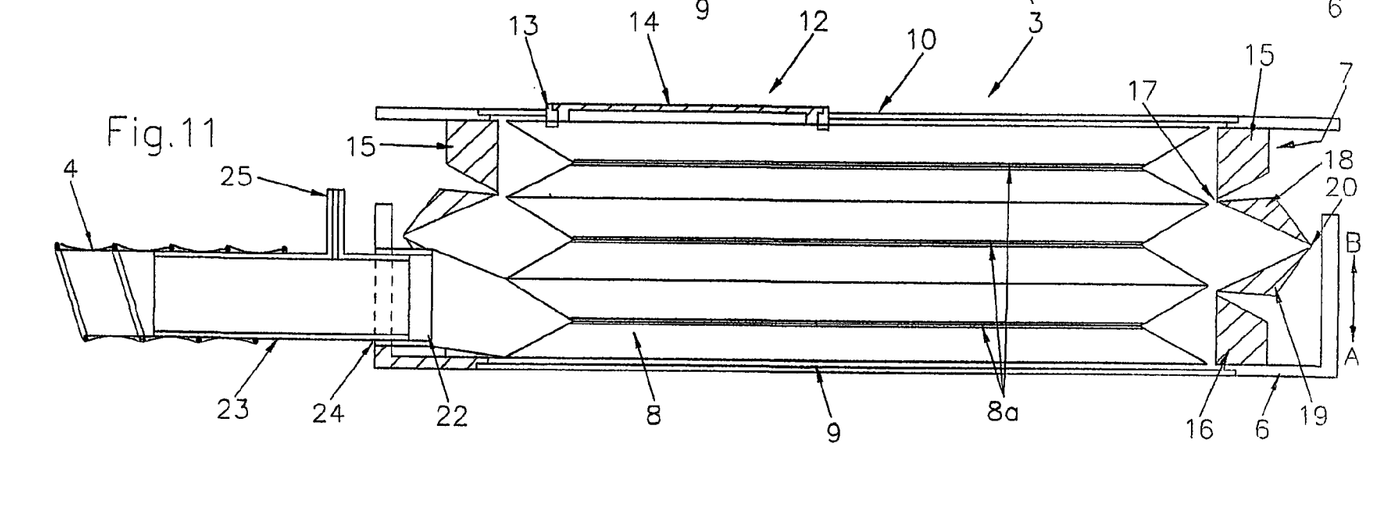

FIGS. 10 and 11 illustrate an alternative form of support framing. As shown in these figures, the support framing described with reference to FIG. 3 is replaced by framing made of hinged strips of material, as described below. The support framing 7 is rectangular in plan, with two longer members mutually parallel and secured at right angles to two shorter members by two sets of four right angle corner pieces 15,16.

Each corner piece 15 is formed with a flat upper surface which is rigidly secured to the inner surface of the side 10. Each corner piece 15 is rectangular in cross-section with the face adjacent the underlying framing members cut away and its lower corner 17 hinged to the corresponding underlying framing members.

Each corner piece 16 has the same shape as the corresponding corner piece 15; the lower surface of each corner piece 16 is rigidly secured to the inner surface of the side 9. The upper corner of each corner piece 16 is hinged to the corresponding framing member.

Each framing member is made up of two complimentary triangular cross-section components (see for example components 18, 19 in FIG. 11) secured together along one apex 20. In the folded down position shown in FIG. 10, the triangular cross-section components fold together to form a parallelogram in cross-section.

The above described support framing operates in the same manner as that shown in FIG. 3 and provides a rigid non distorting hinge which permits movement of the movable side 10 relative to be fixed side 9 only in a single plane, such that during its movement, side 10 always remains parallel to side 9.

Figure 12:
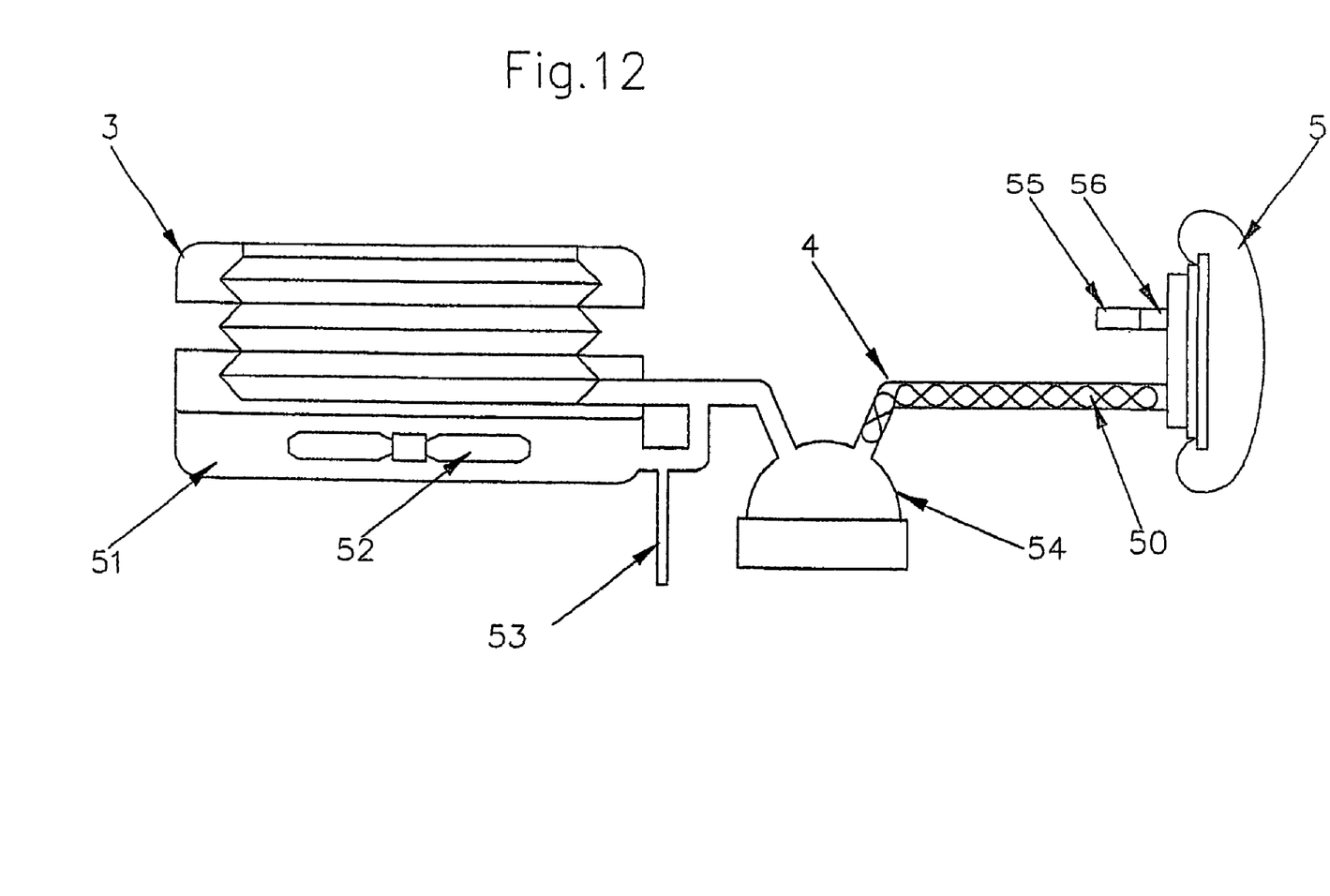
FIG. 12 is a diagrammatic sectional side view of a modified form of the device of the present invention.

A modified version of the device is shown in FIG. 12. Except as specifically described, this modified version is the same as the version first described.

Referring to FIG. 12, an air reservoir apparatus 3 is connected by an air supply hose 4 to a face mask 5. The air supply hose 4 may be heated by a wire 50. The air reservoir apparatus 3 has an extra compartment 51 built into the base of the housing; a multi bladed fan 52 and an associated power unit are mounted in the compartment 51, giving a compact device capable of supplying air with substantially less noise than a conventional compressor.

Air is supplied to the fan 52 through an air intake (not shown) formed in the compartment 51; the intake system may include an air filtering system. If an air/oxygen mix is required rather than plain air, oxygen is supplied to the outlet from the compartment 51 through an inlet 53. The air or air/oxygen mix then fills the reservoir and passes through a humidifier 54 (optional) before entering the mask 5.

The speed of the fan 52 may be preset or manually controlled, but preferably is controlled by pressure sensors which measure the gas flow rate from the fan 52 (e.g. by measuring a pressure drop over a fixed low resistance) and also measure CPAP level by the patient. The sensor measurements are used to control the speed of the fan motor in known manner.

It should be noted that in the equipment of the present invention, preferably the connectors on the ends of all of the components which need to be connected together are formed so that they are keyed to the correct connection only and cannot be incorrectly connected, nor can inappropriate equipment be substituted for the correct components. Thus, one end of the air hose 4 would be formed so that it could be fitted only onto the outer end of the tube 23; the other end of the air hose 4 would be formed so that it could be connected only onto the inlet 26 of the mask 5. Further, the tube 23 and the inlet 26 would be formed so that they could accept only the connectors on the ends of the correct type of air hose 4. The connections between the oxygen supply and the inlet 25 may be keyed in the same manner.

In addition to the uses described above, the device of the present invention also can be used for treating a number of conditions:—

1. The device of the present invention may be used with an air compressor for sleep apnoea patients, who require pressurized air without additional oxygen. At present, the sleep apnoea apparatus consists of a compressor and a face mask or equivalent. Since the present device incorporates a reservoir and low resistance hosing, it can deliver a very constant pressure at low fresh gas flows without the need for high and variable continuous flows which require a powerful (and therefore noisy) compressor.
2. The device of the present invention may be used in combination with a suitable oxygen or air supply in the treatment of high altitude related conditions such as acute pulmonary oedema, altitude sickness, sleep problems caused by high altitude, and breathing problems of critically ill patients during air transport.
3. The device of the present invention may be used to provide a low resistance enhanced oxygen delivery device for use in hyperbaric chambers (recompression tanks), submarines, and for space medicine and hyperbaric medicine use.
4. The device of the present invention may be used for patients who require oxygen enriched air but whose condition is such that CPAP is thought to be unhelpful. In this case, the exhaust valve is replaced by a one-way low resistance valve, and the device is stopped open to allow the reservoir to fill at very low pressures. This gives the patient oxygen enriched air but with a clinically insignificant level of CPAP.
5. The device of the present invention may be used with a two level exhaust valve to provide two levels of CPAP pressure. This technique is known; the changes in CPAP level may be automatic or timed to the patient's respiration.

It will be appreciated that the above-described device is readily portable:—the hose 4 is disconnected from the tube 23, and compressed or coiled. The mounting dip 92 is then pivoted until the plane of the inlet 22 is parallel to the plane of the side 9. The catches 11 are used to hold the plate 10 tightly to the remainder of the housing 6. In this folded-down state, the device is robust and occupies little space.

The invention claimed is:

1. An air reservoir apparatus for a continuous positive airway pressure device, the air reservoir apparatus comprising:
    a rigid housing protecting an air reservoir, wherein the air reservoir is inflatable and is provided with an air inlet and an air outlet, which are combined or separated;
    a plate arranged to apply a uniform pressure on the air reservoir, irrespective of the degree of inflation of the air reservoir;
    said plate being connected to the housing by substantially non distorting expandable framing, which can expand or contract to permit movement of the plate only in a single plane, as the air reservoir respectively inflates or deflates.

2. The apparatus as claimed in claim 1, wherein said plate is securable to said housing when the air reservoir is deflated, and is dimensioned and arranged to form one side of the housing, such that the air reservoir is completely enclosed by the combination of the plate and the housing when the plate is secured to the housing.

3. The apparatus as claimed in claim 2, wherein said plate is a solid sheet.

4. The apparatus as claimed in claim 1, wherein said plate is formed with a sealable access port for access to said air reservoir, such that the reservoir can be inserted and removed through said port.

5. The apparatus as claimed in claim 1, wherein said air reservoir is made of a flexible but non-elastic material.

6. The apparatus as claimed in claim 5, wherein said air reservoir is made of a transparent material.

7. The apparatus as claimed in claim 5, wherein said air reservoir is formed with a series of concertina pleats around its periphery, such that the deflated reservoir can lie substantially flat but the inflated reservoir retains its shape.

8. The apparatus as claimed in claim 7, wherein each said concertina pleat is reinforced by a stiffening rib.

9. The apparatus as claimed in claim 7, wherein the air reservoir is internally reinforced by a series of spaced internal webs which are designed to be under tension when the reservoir is inflated.

10. The apparatus as claimed in claim 1, wherein said uniform pressure is applied to the air reservoir by means of the plate.

11. The apparatus as claimed in claim 10, wherein at least part of said uniform pressure is applied to the air reservoir by means of weights secured to the plate.

12. The apparatus as claimed in claim 1, wherein said uniform pressure is applied to the air reservoir by means of a springloaded drum mounted on the side of the plate opposite to said air reservoir, the drum being connected to the housing by non elastic cables such that the plate is biased towards the housing and thus applies pressure to the air reservoir.

13. The apparatus as claimed in claim 12, wherein said springloaded drum is calibrated so that the pressure applied to the air reservoir by the plate can be accurately adjusted.

14. The apparatus as claimed in claim 1, wherein said framing comprises a pair of spaced-apart frames, the planes of the frames being parallel to each other and perpendicular to the plane of movement of the plate; the frames being connected together by a plurality of spaced pivots which are designed to permit relative movement of said frames only in said plane of movement of the plate; one of said frames being rigidly secured to the plate and the other of said frames being rigidly secured to said housing.

15. The apparatus as claimed in claim 14, wherein each frame comprises: a plurality of spaced blocks connected by rods rotatably secured thereto; and each pivot comprises a pair of hinge arms, one of said arms in each pair being pivoted at one end to one rod of one frame and at the other end to the other arm of that pair, and the other of said arms in each pair being pivoted at one end to one rod of the other frame and at the other end to the other arm of that pair.

16. The apparatus as claimed in claim 15, wherein the plate and the housing are secured to the respective frames by means of the blocks of that frame.

17. A method of medical treatment for any condition treatable by means of a metered dose inhalation agent, comprising:
(1) providing a continuous positive airway pressure device which incorporates an air reservoir apparatus as claimed in claim 1 and which also includes an air supply hose having an internal diameter in the range 30-55 mm which connects the air reservoir to a face mask incorporating a threshold resistor exhaust valve;
(2) connecting said device to a suitable supply of air;
(3) connecting to said air supply hose means for dispensing an appropriate metered dose inhalation agent at a predetermined rate;
(4) administering said agent to a patient in the airstream delivered through the face mask by said device.

18. The method as claimed in claim 17, wherein said metered dose inhalation agent is selected from the group consisting of: bronchodilators; gene therapy agents; proteins; peptides; macromolecules.

19. A method of treatment for sleep apnea comprising:
(1) providing a continuous positive airway pressure device which incorporates an air reservoir apparatus as claimed in claim 1 and which also includes an air supply hose having an internal diameter in the range of 30 to 55 mm which connects the air reservoir to a delivery device;
(2) connecting said device to an air compressor;
(3) administering pressurized air to a patient via the delivery device.

20. A method of medical treatment of altitude sickness, acute pulmonary edema or conditions requiring hyperbaric treatment, comprising:
(1) providing a continuous positive airway pressure device which incorporates an air reservoir apparatus as claimed in claim 1 and which also includes an air supply hose having an internal diameter in the range 30 to 55 mm which connects the air reservoir to a delivery device;
(2) connecting said CPAP device to a suitable supply of air;
(3) administering said air to a patient through said delivery device.

21. The method as claimed in claim 20 wherein said delivery device is selected from the group consisting of: face mask, nasal mask, mouthpiece, endotracheal or tracheotomy tube.

22. The apparatus as claimed in claim 1, wherein said framing includes sets of hinged strips of material, one strip of each set being pivotally secured to said plate, and the other strip of each set being pivotally secured to said housing; the strips of each set being hinged to each other.

23. A continuous positive airway pressure device including: air reservoir apparatus as claimed in claim 1 or claim 22, connected by an air supply hose to a delivery device.

24. The device as claimed in claim 23, wherein the air inlet/outlet of the air reservoir is a push-fit connection to the air supply hose.

25. The device as claimed in claim 23, wherein the air inlet/outlet of the air reservoir is releasably held in a mounting clip pivoted to the housing such that the plane of the air inlet/outlet may be pivoted between an out-of-use position in which said plane lies approximately in the plane of the plate, and an in-use position perpendicular thereto; and the air supply hose is releasably connectable to said mounting clip.

26. The device as claimed in claim 25, wherein in said out-of-use position, the mounting clip is arranged to clip over the edge of the housing.

27. The device as claimed in claim 23, wherein the delivery device is selected from the group consisting of: face mask; nasal mask; mouthpiece; endotracheal or tracheotomy tube.

28. The device as claimed in claim 23, wherein the delivery device comprises a face mask incorporating an exhaust valve.

29. The device as claimed in claim 28, wherein the exhaust valve is a threshold resistor valve.

30. The device as claimed in claim 28, wherein the exhaust valve is a fixed orifice valve.

31. The device as claimed in claim 23, wherein at least part of the air supply hose is heated.

32. The device as claimed in claim 23, further including a humidifier arranged to humidify at least part of the incoming air in use.

33. The device as claimed in claim 23, further including a fan arranged in use to supply air to the reservoir at above-atmospheric pressure.

34. The device as claimed in claim 23, wherein each of the connections between the air reservoir apparatus, the air supply hose, and the delivery device is keyed to provide a unique connection.

35. The device as claimed in claim 23, wherein the air supply hose has an internal diameter in the range 30-55 mm.

* * * * *